(12) United States Patent
Gebert-Schwarzwaelder et al.

(10) Patent No.: US 10,821,063 B2
(45) Date of Patent: Nov. 3, 2020

(54) METHOD FOR DECOLORIZING DYED KERATINIC FIBERS

(71) Applicant: Henkel AG & Co. KGaA, Duesseldorf (DE)

(72) Inventors: Antje Gebert-Schwarzwaelder, Neuss (DE); Helmut Giesa, Meerbusch (DE); Astrid Kroos, Monheim (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 99 days.

(21) Appl. No.: 15/839,855

(22) Filed: Dec. 13, 2017

(65) Prior Publication Data
US 2018/0161261 A1  Jun. 14, 2018

(30) Foreign Application Priority Data

Dec. 14, 2016 (DE) .................. 10 2016 225 047

(51) Int. Cl.
A61Q 5/08 (2006.01)
A61K 8/46 (2006.01)

(52) U.S. Cl.
CPC .............. A61K 8/46 (2013.01); A61Q 5/08 (2013.01); A61K 2800/88 (2013.01)

(58) Field of Classification Search
None
See application file for complete search history.

(56) References Cited

U.S. PATENT DOCUMENTS 3,892,845 A    7/1975   Cunningham et al.
3,993,436 A   11/1976   Fujinuma
5,651,960 A    7/1997   Chan et al.
5,652,960 A    8/1997   Kaknevicius
2002/0166182 A1  11/2002  Bhagyalakshmi et al.
2008/0085249 A1   4/2008  Cannell et al.

FOREIGN PATENT DOCUMENTS

EP    1300136 A2    4/2003
FR    2252841 A1    6/1975
WO    2008055756 A1 5/2008

OTHER PUBLICATIONS

Intellectual Property Office, Search Report under Section 17(5) for United Kingdom Patent Application No. GB1720644.2 dated Oct. 1, 2018.

Primary Examiner — Jyothsna A Venkat
(74) Attorney, Agent, or Firm — Lorenz & Kopf, LLP

(57) ABSTRACT

A method, usage and kit-of-parts for decolorizing human keratin fibers, which were colored with oxidation dyes and/or partially-oxidizing dyes, comprising the application of an agent to the dyed keratin fibers, which contains in a cosmetic carrier at least one compound of the Formula (I)

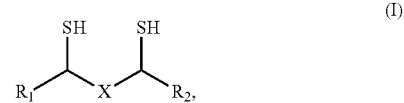

wherein
X denotes a bivalent organic radical of the Formula (II) or a direct bond,

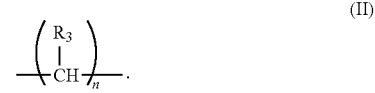

10 Claims, No Drawings

METHOD FOR DECOLORIZING DYED KERATINIC FIBERS

CROSS-REFERENCE TO RELATED APPLICATION

This application claims priority to German Patent Application No. 10 2016 225 047.7, filed Dec. 14, 2016, which is incorporated herein by reference in its entirety.

TECHNICAL FIELD

The present disclosure relates to the cosmetic sector. The subject matter of the present disclosure is a method for the reductive decolorization of dyed human keratin fibers. This method involves applying a cosmetic agent, which contains at least one special dithio compound of a Formula (I) and which is essentially free of further reducing agents, to the keratin fibers, which were previously dyed with oxidation dyes and/or partially-oxidizing dyes.

BACKGROUND

A further subject matter of the present disclosure is a kit-of-parts, by employing which the composition used in the method can be produced. The use of dithio compounds of the Formula (I) for the reductive decolorization of dyed human hair is a further subject matter of the present disclosure.

Preparations for tinting and coloring hair are an important type of cosmetic agent. They can serve to tint the natural hair color to a lesser or greater degree depending on the preferences of each and every person, achieve a completely different hair color or cover unwanted color shades, such as shades of gray, for example. Routine hair dyes are formulated either on the basis of oxidation dyes or on the basis of partially-oxidizing dyes, depending on the preferred color and/or permanency of the dye. To achieve special tints, combinations of oxidation dyes and partially-oxidizing dyes are also frequently used.

Dyes formulated on the basis of oxidation dyes lead to brilliant and permanent color shades. However, they do require the use of strong oxidants, such as hydrogen peroxide solutions, for example. Said dyes contain oxidative dye precursors, so-called developer components and coupler components. The developer components join together or couple with one or more coupler components to form, under the influence of oxidants or atmospheric oxygen, the actual colorants per se.

Dyes formulated on the basis of partially-oxidizing dyes are often used for achieving temporary colors. Partially-oxidizing dyes are dye molecules that coat the hair itself and do not require an oxidative process to create the color. Important representatives of this dye class include triphenylmethane dyes, azo dyes, anthraquinone dyes or nitrobenzene dyes, each of which can carry cationic or anionic groups.

With all said dyeing methods, however, the color may need to be reversed, either whole or in part, for various reasons. A partial removal of the color may be the ideal solution, for example, if the color result has a darker effect on the fibers than desired. On the other hand, a complete removal of the color may be desired in some cases. It is conceivable, for example, that the hair is to be colored or tinted in a particular way for a specific occasion, and the original color is to be restored after a few days.

Technical literature also discloses decolorizing agents and methods. The oxidative post-treatment of dyed hair, by employing a routine blonding agent for example, is a well-known method from the prior art. With this process, however, the fibers can also be damaged through the use of strong oxidants.

Moreover, reductive processes for decolorization have already been described. European Patent Application EP 1 300 136 A2 discloses, for example, a method for hair treatment, wherein the hair is colored in a first step and then reductively decolorized again in a second step. Said reductive decolorization is achieved by employing a formulation containing a diothine salt and a surfactant. In WO 2008/055756 A2, the reductive decolorization of keratin fibers is achieved using a mixture formed from a reducing agent and an absorption agent.

Another decolorizing agent well known from the prior art is Rongalit (hydroxymethane sulfinic acid), which is commercially available in the form of its sodium salt (sodium hydroxymethane sulfinate), for example. Rongalit has an outstanding decolorizing effect. For toxicological reasons, however, the use of said substance is avoided wherever possible.

When reductive decolorizing agents are used, the decolorization effect is achieved by reducing the dyes located on the keratin fibers and/or hair. The reduction process usually involves converting the dyes to their reduced forms and/or leuco forms. This method involves reducing the double bonds present in the dyes, thus interrupting the chromophoric system of the dyes and converting the dye into a colorless form.

A general problem with the reductive decolorizing agents known from the prior art is that although the dyed keratin fibers can be decolorized by employing the reducing agent, said decolorizing is not long-lasting. Particularly in the case of oxidatively colored hair, where the coloration is produced by oxidative dye precursors of the developer and coupler type, colors with very good fastness properties can be attained in some cases. When the reductive decolorizing agent is applied, said dyes are now reductively converted to uncolored compounds—which, due to similarly good fastness properties, however, remain on the hair as before. Once the reducing agent has been rinsed out and, when exposed to atmospheric oxygen, these reduced forms can now be gradually reverse-oxidized. Said reverse-oxidization process causes a reverse-coloration effect to a greater or lesser degree. Said reverse colorization effect does not usually correspond to the shade to which the keratin fibers were previously colored. Instead, it can have a greater or lesser unattractive effect and is therefore not desired by the users of the dye.

The present disclosure therefore addressed the problem of providing a method for decolorizing dyed keratinic fibers, which decolorizes the dyed keratin fibers to the greatest possible degree. The decolorizing effect should be long-lasting, and the decolorized keratin fibers should, under the effect of atmospheric oxygen, not suffer any reverse colorization, no tint shift and no post-darkening. The decolorizing agent ought to have a good decolorizing effect, particularly on the keratin fibers, which were dyed previously with oxidative dyes on the basis of oxidation dye precursors of the developer and/or coupler type. Moreover, the decolorizing agent is to be toxicologically harmless.

As part of the work leading to this present disclosure, it unexpectedly emerged that keratin fibers can be excellently decolorized if a cosmetic agent containing at least one special dithio compound (and/or dimercapto compound) of the Formula (I) is applied to the previously dyed hair.

BRIEF SUMMARY

Methods, uses, and compounds for decoloring keratin fibers are provided. In an exemplary embodiment, a method includes applying an agent to dyed keratin fibers, where the keratin fibers were dyed with oxidation dyes and/or partially-oxidizing dyes. The agent includes, in a cosmetic carrier, at least one compound of Formula (I),

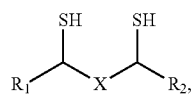

wherein
R1, R2 denote, independently of one another, a hydrogen atom, a carboxy group (—COOH) or the salt thereof, a C1-C6 alkyl group, a hydroxy C1-C6 alkyl group, or a C1-C6 alkoxy-carbonyl group. X denotes a bivalent organic radical of the Formula (II) or a direct bond,

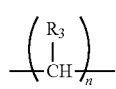

R3 denotes a hydroxy group, a hydrogen atom, a carboxy group (—COOH) or the salt thereof, a C1-C6 alkoxy-carbonyl group, a C1-C6-alkyl group or an amino group, and n denotes an integer from 1 to 4. The total content of sulfur-containing compounds which are not the same as compounds of Formula (I) is below about 1.0 wt. %, relative to a total weight of the agent.

A use of compounds for decoloring human keratin fibers dyed with oxidation and/or partially oxidizing agents is described in another embodiment. The compounds are of Formula (I),

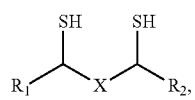

wherein
R1, R2 denote, independently of one another, a hydrogen atom, a carboxy group (—COOH) or the salt thereof, a $C_1$-$C_6$ alkyl group, a hydroxy $C_1$-$C_6$ alkyl group, or a $C_1$-$C_6$ alkoxy-carbonyl group,
X denotes a bivalent organic radical of the Formula (II) or a direct bond,

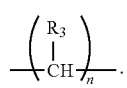

where R3 denotes a hydroxy group, a hydrogen atom, a carboxy group (—COOH) or the salt thereof, a $C_1$-$C_6$ alkoxy-carbonyl group, a $C_1$-$C_6$-alkyl group or an amino group, and n denotes an integer from 1 to 4.

A kit-of-parts is provided in another embodiment. The kit-of-parts is for decolorizing human keratin fibers that were dyed with oxidation and/or partial oxidation dyes, and includes a Preparation (A) and a Preparation (B) that are separately packaged. Preparation (A) includes, in a cosmetic carrier, at least one compound of Formula (I),

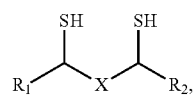

wherein R1, R2 denote, independently of one another, a hydrogen atom, a carboxy group (—COOH) or the salt thereof, a $C_1$-$C_6$ alkyl group, a hydroxy $C_1$-$C_6$ alkyl group, or a $C_1$-$C_6$ alkoxy-carbonyl group. X denotes a bivalent organic radical of the Formula (II) or a direct bond

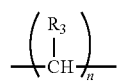

and R3 denotes a hydroxy group, a hydrogen atom, a carboxy group (—COOH) or the salt thereof, a $C_1$-$C_6$ alkoxy-carbonyl group, a $C_1$-$C_6$-alkyl group or an amino group, and n denotes an integer from 1 to 4. Preparation (B) is hydrous and includes at least one acid and/or at least one alkalizing agent.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

A first subject matter of the present disclosure is a method for decolorizing human keratin fibers, which were colored with oxidation dyes and/or partially-oxidizing dyes, comprising the application of an agent to the dyed keratin fibers, which (a) contains in a cosmetic carrier at least one compound of the Formula (I)

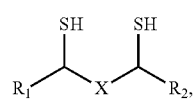

wherein
R1, R2 denote independently of one another a hydrogen atom, a carboxy group (—COOH) or the salt thereof, a $C_1$-$C_6$ alkyl group, a hydroxy $C_1$-$C_6$ alkyl group, or a $C_1$-$C_6$ alkoxy-carbonyl group, X denotes a bivalent organic radical of the Formula (II) or a direct bond,

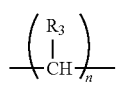

R3 denotes a hydroxy group, a hydrogen atom, a carboxy group (—COOH) or the salt thereof, a $C_1$-$C_6$ alkoxy-carbonyl group, a $C_1$-$C_6$-alkyl group or an amino group, and
n denotes an integer from 1 to 4, and
(b) the total content of sulfur-containing compounds, which are not the same as the compounds of Formula (I), is below 1.0 wt. %, wherein the total content is relative to the total weight of the agent.

The application of the decolorizing agent as contemplated herein achieves—depending on the dyes previously used for the dyeing process—an almost complete or even complete decolorization of previously dyed keratin fibers. The decolorization agent has an outstanding effect, above all on keratin fibers previously dyed with oxidation dyes. Particularly, it has unexpectedly emerged that said decolorizing effects lasts even after the reducing agent has been rinsed out, and that the decolorized keratin fibers, which are exposed to the effect of atmospheric oxygen for hours and/or days, suffer hardly any reverse oxidation and no post-darkening.

Human keratin fibers mean in particular human hair.

Method for the Decolorization of Dyed Hair

The expression "dyed keratinous fibers" means keratin fibers, which were dyed by employing conventional cosmetic dyes known to a person skilled in the art. Said dyes are oxidation dyes (developer and coupler) and/or partially-oxidizing dyes. In this context, explicit reference is made to the known monographies, e.g. Kh. Schrader, Grundlagen and Rezepturen der Kosmetika [Cosmetic principles and formulas, 2nd Edition], Hüthig Buch Verlag, Heidelberg, 1989, which reflect the corresponding knowledge of a person skilled in the art.

The agents used in the method contain the compound(s) of the Formula (I) used in the method in a cosmetic carrier, in a hydrous or hydrous-alcohol carrier, for example. Carriers such as creams, emulsions, gels or surfactant-containing foaming solutions, such as shampoos, foaming aerosols, foam formulations or other preparations suitable for application on the hair, are used for the purpose of reductive decolorization. Agents for the reductive decolorization of keratinic fibers are preferably creams, emulsions or free-flowing gels.

The method as contemplated herein is a method for the decolorization of human keratin fibers. The aim of the method is to remove the artificial dyes previously applied in the dyeing method—and now no longer desired—from the keratin fibers again and/or convert said dyes to a colorless form. For this purpose, the hair previously dyed with oxidation dyes and/or partially-oxidizing dyes are treated with a decolorizing agent. The decolorizing agent contains at least one compound of the Formula (I). The decolorizing agent can be applied to the keratin fibers (hair) either manually by employing a gloved hand, or also using a brush, an applicator or an applicator bottle and/or an applicator container.

That the decolorizing agent (and/or color dye removal agent) is applied to keratin fibers, which are still colored by employing artificial dyes, is essential to the method as contemplated herein. The dyes can be present in and/or on the outer layer of the hair (cuticula) or also inside the hair (cortex).

The precise time at which the decolorization method is applied depends on the time at which the user wishes to remove the (artificially produced) hair dye. Therefore, the decolorization method as contemplated herein can be applied immediately after a (possibly failed) dyeing process, or also at a later time. If the decolorization method is applied at a later time, the hair can be washed one or more times between the colorization and the decolorization processes. Depending on the number of hair washes, the dye—now no longer required—may have already been washed out somewhat, and therefore the user now also removes the remaining dyes by applying the method as contemplated herein.

Compound of the Formula (I)

The method as contemplated herein comprises the application of a cosmetic agent, which (a) contains, as the essential component, at least one compound of the Formula (I)

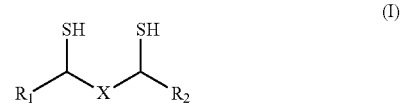

wherein
R1, R2 denote independently of one another a hydrogen atom, a carboxy group (—COOH) or the salt thereof, a $C_1$-$C_6$ alkyl group, a hydroxy $C_1$-$C_6$ alkyl group, or a $C_1$-$C_6$ alkoxy-carbonyl group,
X denotes a bivalent organic radical of the Formula (II) or a direct bond,

R3 denotes a hydroxy group, a hydrogen atom, a carboxy group (—COOH) or the salt thereof, a $C_1$-$C_6$ alkoxy-carbonyl group, a $C_1$-$C_6$-alkyl group or an amino group, and
n denotes an integer from 1 to 4.
Examples of the substituents R1, R2 and R3 stated in the Formula (I) are shown below:
Examples of $C_1$-$C_6$-alkyl groups are —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$(CH_2)_4CH_3$, —$(CH_2)_5CH_3$. Even more preferred alkyl radicals are methyl and ethyl.
Examples of hydroxy-$C_1$-$C_6$-alkyl groups are —$CH_2$—OH, —$CH_2$—$CH_2$—OH, —$CH_2$—$CH_2$—$CH_2$—OH, —$CH_2$—CH(OH)—$CH_3$, —$CH_2$—$CH_2$—$CH_2$—$CH_2$—OH, the groups —$CH_2$—OH and —$CH_2$—$CH_2$—OH being particularly preferred.
Examples of $C_1$-$C_6$-alkoxy-carbonyl groups are the methoxycarbonyl group (—C(O)$OCH_3$) and the ethoxycarbonyl group (—C(O)$OCH_2CH_3$).

The carboxyl group is the group —COOH. The hydrogen atom of the carboxyl group is acidic, and therefore the (protonated) carboxyl group—more particularly in a hydrous cosmetic carrier—can also be in equilibrium with its deprotonated form. Using the carboxy group in the form of its salt, such as sodium carboxylate (—COONa), potassium carboxylate (—COOK) and/or ammonium carboxylate (—COO(NH₄)) is likewise as contemplated herein.

In the compounds of the Formula (I), radicals R1 and R2 denote independently of one another a hydrogen atom, a carboxy group (—COOH) or the salt thereof, a $C_1$-$C_6$-alkyl group, a hydroxy-$C_1$-$C_6$-alkyl group, or a $C_1$-$C_6$-alkoxy-carbonyl group.

Since radicals R1 and R2 denote, independently of one another, the aforementioned radicals, R1 and R2 can be the same or different in a compound of the Formula (I).

It has been shown that the compounds of the Formula (I), in which R1 and R2 denote independently of one another a hydrogen atom or a carboxy group, have the best decolorizing effect. Therefore, applying an agent containing at least one compound of the Formula (I), wherein R1 and R2 denote, independently of one another, a hydrogen atom or a carboxy group (—COOH) (and/or the salt thereof) is particularly preferred in the method as contemplated herein.

In a most preferred embodiment, a method as contemplated herein is exemplified in that an agent containing at least one compound of the Formula (I) is applied to the dyed keratin fibers, wherein
R1, R2 denote, independently from one another, a hydrogen atom or a carboxy group (—COOH) or the salt thereof.

In another most preferred embodiment, radicals R1 and R2 denote identical substituents.

In a most preferred embodiment, a method as contemplated herein is exemplified in that an agent containing at least one compound of the Formula (I) is applied to the dyed keratin fibers, wherein
R1, R2 both denote a hydrogen atom.

In the compounds of the Formula (I), X denotes either a bivalent organic radical of the Formula (II) or a direct bond

(II)

The grouping of the Formula (II) is a bivalent radical, i.e. the radical placed between parentheses is bound—via the bond drawn on the left and on the right respectively—to the C-atoms of the Formula (I) carrying the thiol group.

The radical n can denote an integer from 1 to 4 and indicates the number of units—CH(R₃)— comprising the structural unit (II).

Where n denotes 1 (and R₃ a hydrogen atom), the grouping of Formula (II) is a methylene group.

Where n denotes 2 (and R₃ a hydrogen atom), the grouping of Formula (II) is an ethylene group.

Thus, where X denotes a grouping of the Formula (II), the compounds as contemplated herein are compounds of the Formula (Ia)

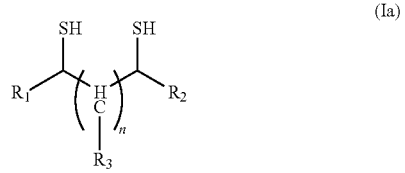

(Ia)

Radical R3 denotes a hydroxy group, a hydrogen atom, a carboxy group (—COOH) or the salt thereof, a $C_1$-$C_6$-alkoxy-carbonyl group, a $C_1$-$C_6$-alkyl group or an amino group.

In decolorizing tests, the compounds of the Formula (I), wherein X denotes a bivalent organic radical of the Formula (II) and the radical R3 denotes a hydroxy group or a hydrogen atom, have proven particularly potent. Explicitly most preferably, R3 denotes a hydroxy group.

In another most preferred embodiment, a method as contemplated herein is exemplified in that an agent containing at least one compound of the Formula (I) is applied to the dyed keratin fibers, wherein
X denotes a bivalent organic radical of the Formula (II),

(II)

and
R3 denotes a hydroxy group or a hydrogen atom.

In decolorizing tests, the compounds of the Formula (I), wherein X denotes a bivalent organic radical of the Formula (II) and n denotes the number 2 or 3, have proven particularly effective. Explicitly most preferably, n denotes the number 2.

In another most preferred embodiment, a method as contemplated herein is exemplified in that an agent containing at least one compound of the Formula (I) is applied to the dyed keratin fibers, wherein
X denotes a bivalent organic radical of the Formula (II),

(II)

and
n denotes the number 2 or 3, more preferably the number 2.

Moreover, the compounds of the Formula (I), wherein the radical X denotes a direct bond, have proven highly suitable. Where X denotes a direct bond, the compounds as contemplated herein are compounds of the Formula (Ib)

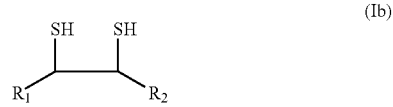

(Ib)

Certain compounds of the Formula (I) are able to achieve a particularly good decolorization of artificially-dyed hair. Therefore, the use of one or more compounds from the following group is most preferred

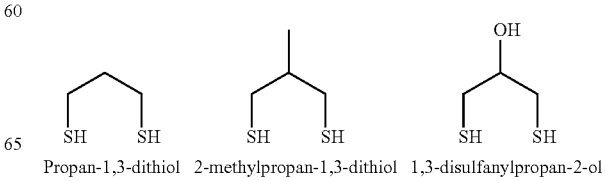

Propan-1,3-dithiol   2-methylpropan-1,3-dithiol   1,3-disulfanylpropan-2-ol

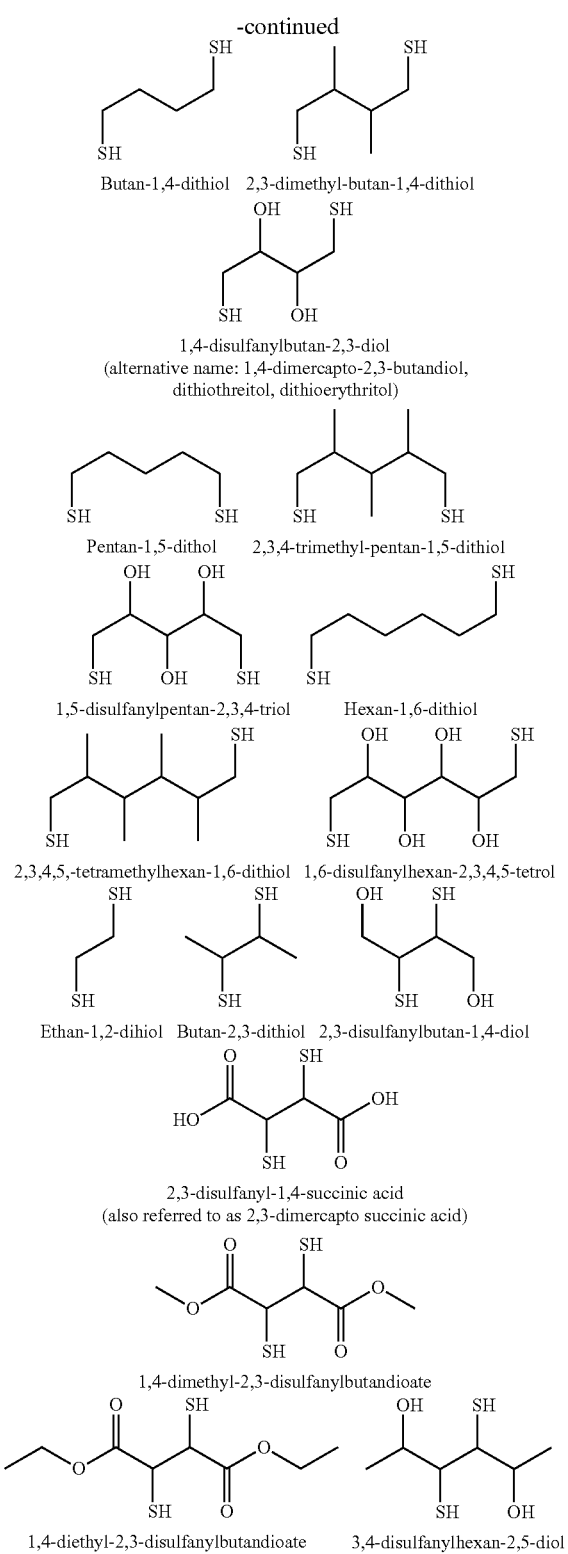

In a particularly preferred embodiment, an agent as contemplated herein is exemplified in that (a) contains at least one compound of the Formula (I), which is selected from the group of
1,3-disulfanylpropan-2-ol
1,4-disulfanylbutan-2,3-diol (1,4-dimercapto-2,3-butandiol, dithiothreitol, dithioerythritol)
1,5-disulfanylpentan-2,3,4-triol
2,3-disulfanylbutan-1,4-diol
2,3-disulfanyl-1,4-succinic acid (dimercapto succinic acid)
1,4-dimethyl-2,3-disulfanylbutandioate
1,4-diethyl-2,3-disulfanylbutandioate Most of all and explicitly most preferred is 1,4-disulfanylbutan-2,3-diol (1,4-dimercapto-2,3-butandiol, dithiothreitol, dithioerythritol).

The compounds of Formula (I) as contemplated herein can—depending on the substitution method thereof—contain one or more carbon atoms, which carry 4 different substituents. If this is the case, a compound of the Formula (I) can occur in the form of various stereoisomers. Essentially, stereoisomers have the same structure (i.e. constitution)—and hence the same molecular formula—but differ in the spatial arrangement (configuration) of the atoms.

For example, dithiothreitol (1,4-disulfanylbutan-2,3-diol) can occur in the form of two stereoisomers, in the (2S,3S)-form and in the (2R,3R)-form. Moreover, 1,4-disulfanylbutan-2,3-diol also occurs in a form known as dithioerythritol or dithioerythrit, this being the meso-form.
This present disclosure explicitly comprises all stereoisomers.

The compound(s) of the Formula (I) are used in the agent as contemplated herein in specific quantity ranges. A decolorizing effect can be observed from small application quantities. To obtain an adequate and strong decolorizing effect, however, it is advantageous for the decolorizing agent to contain one or more dithio compounds of the Formula (I) in a total quantity from about 0.1 to about 30.0 wt. %, preferably from about 0.2 to about 20.0 wt. %, more preferably from about 0.3 to about 10.0 wt. % and most preferably from about 0.5 to about 6.0 wt. %. The calculation basis for the quantity values in wt. % is the total weight of all reducing agents of the Formula (I) contained in the agent, said reducing agents being used relative to the total weight of the agent.

In a further most preferred embodiment, a method as contemplated herein contains—relative to the total weight thereof—(a) one or more carboxylic acid esters of the formula (I) in a total quantity of from about 0.1 to about 3.5 wt. %, preferably from about 0.2 to about 2.4 wt. %, more preferably from about 0.3 to about 1.8 wt. % and most preferably from about 0.4 to about 1.2 wt. %.

Content of Other Sulfur-Containing Compounds in the Agent

Another feature essential to the present disclosure of the agent used in the method is that said agent (b) is substantially free of all other sulfur-containing compounds, more particularly reducing agents, which are different from the compounds of the Formula (I).

According to the present disclosure, the expressions "free of sulfur-containing reducing agents" and/or "free of sulfur-containing compounds" mean that no other sulfur-containing reducing agents are used in the agent for the purpose of decolorization. In this way, toxicologically disadvantageous effects for the user can be avoided.

The method as contemplated herein is therefore a method for decolorizing human keratin fibers, which were dyed by employing oxidation dyes and/or partially-oxidizing dyes, wherein the method comprises the application of an agent, the total content of sulfur-containing compounds of which, said compounds being different to the compounds of the Formula (I), being below about 1.0 wt. %. The calculation basis is the total content of all other sulfur-containing compounds, which differ from the compounds (I), contained in the agent. This total content is set relative to the total weight of the agent.

As contemplated herein, a sulfur-containing compound, which differs from the compounds of the Formula (I), is any inorganic and organic substance, the structure of which is inconsistent with the proportions of Formula (I) and the structure of which contains at least one sulfur atom. More particularly, the sulfur-containing compounds, which differ from the compounds of the Formula (I), are sulfur-containing reducing agents.

The reducing agents which differ from the compounds of the Formula (I) include sodium dithionite, zinc dithionite, potassium dithionite, sodium sulfite, sodium hydrogen sulfite, potassium sulfite, potassium hydrogen sulfite, ammonium sulfite, sodium thiosulfate, potassium thiosulfate, ammonium thiosulfate, sodium disulfite, potassium disulfite, ammonium disulfite, hydroxymethane sulfinic acid, sodium methane sulfinate, potassium methane sulfinate, zinc methane sulfinate, aminomethane sulfinic acid, cysteine, thio lactic acid and thioglycol acid (alternative name: sulfanyl acetic acid).

Sodium dithionite is an inorganic reducing agent and has the empirical formula $Na_2S_2O_4$ and CAS No. 7775-14-6.
Zinc dithionite is an inorganic reducing agent and has the empirical formula $ZnS_2O_4$ and CAS No. 7779-86-4.
Potassium dithionite is an inorganic reducing agent and has the empirical formula $K_2S_2O_4$ and CAS No. 14293-73-3.
Sodium sulfite is an inorganic reducing agent and has the empirical formula $Na_2SO_3$ and CAS No. 7757-83-7.
Sodium hydrogen sulfite is an inorganic reducing agent and has the empirical formula $NaHSO_3$ and CAS No. 7631-90-5. Sodium hydrogen sulfite is preferably used in the form of a hydrous solution.
Potassium sulfite is an inorganic reducing agent and has the empirical formula $K_2SO_3$ and CAS No. 10117-38-1.
Potassium hydrogen sulfite is an inorganic reducing agent and has the empirical formula $KHSO_3$ and CAS No. 7773-03-7.
Ammonium sulfite is an inorganic reducing agent and has the empirical formula $(NH_4)_2SO_3$ and CAS No. 10196-04-0.
Sodium thiosulfate is an inorganic reducing agent and has the empirical formula $Na_2S_2O_3$ and CAS No. 7772-98-7.
Potassium thiosulfate is an inorganic reducing agent and has the empirical formula $K_2S_2O_3$ and CAS No. 10294-66-3.
Ammonium thiosulfate is an inorganic reducing agent and has the empirical formula $(NH_4)_2S_2O_3$ and CAS No. 7783-18-8.

Hydroxymethane sulfinic acid is an inorganic reducing agent and has the empirical formula $HO-CH_2-S(O)OH$ and CAS No. 79-25-4. Hydroxymethane sulfinic acid is also referred to as formaldehyde sulfoxylic acid.

Amino methane sulfinic acid is an inorganic reducing agent and has the empirical formula $H_2N-CH_2-S(O)OH$ and CAS No. 118201-33-5.

As contemplated herein cysteine (2-amino-3-sulfanyl propionic acid) means D-cysteine, L-cysteine and/or a mixture of D- and L-cysteine.

Thio lactic acid (2-sulfanylpropionic acid) means D-thio-lactic acid, L-thio-lactic acid and/or a mixture of D- and L-thio lactic acid.

Ammonium thiolactate is the ammonium salt of thio lactic acid (i.e. the ammonium salt of 2-sulfanylpropionic acid)

Thioglycol acid (sulfanyl acetic acid, 2-mercapto-acetic acid) means an organic reducing agent, which has the formula $HS-CH_2-COOH$ and the CAS No. 68-11-1.

Ammonium thioglycolate is the ammonium salt of thiglycol acid (i.e. the ammonium salt of 2-sulfanyl acetic acid)

As contemplated herein, the total content of all sulfur-containing compounds, which differ from the compounds of the Formula (I), more particularly the aforementioned reducing agent, is below about 1.0 wt. %. Preferably, however, even smaller quantities of all other reducing agents are used.

In another, most preferred embodiment, a method as contemplated herein is exemplified in that an agent, the total content of sulfur-containing compounds of which are different to the compounds of the Formula (I), is below about 0.5 wt. %, preferably below about 0.1 wt. % and more preferably below about 0.05 wt. %, the total content being relative to the total weight of the agent, is applied to the dyed keratin fibers.

The agents as contemplated herein also contain at least one surfactant from the group of anionic, amphoteric, zwitterionic, non-ionic and/or cationic surfactants.

In another most preferred embodiment, a method as contemplated herein is exemplified in that an agent containing at least one surfactant from the group of anionic, amphoteric, zwitterionic, non-ionic and/or cationic surfactants is applied to the dyed keratin fibers.

Surfactants are amphiphilic (bifunctional) compounds that include at least one hydrophobe and at least one hydrophile molecular part. The hydrophobic radical is preferably a hydrocarbon chain with from about 8 to about 24 carbon atoms, which can be saturated or unsaturated, linear or branched. This $C_8$-$C_{24}$ alkyl chain is most preferably linear.

Accordingly, preferred anionic surfactants are exemplified by the presence of a water-solubilizing anionic group, such as a carboxylate or phosphate group and a lipophilic alkyl group having approximately 8 to 30 carbon atoms. Furthermore, the molecule can contain glycol or polyglycol ether groups, ester, ether and amide groups, as well as hydroxyl groups.

Typical examples of anionic surfactants are mono and dialkyl sulfosuccinates, mono and amide soaps, ether carboxylic acids and the salts thereof, fatty acid ethionates, fatty acid sarcosinates, fatty acid taurides, acyllactylates, acyltartrates, acylglutamates, acylaspartates, protein fatty acid condensates (more particularly wheat-based plant products) and alkyl(ether)phosphates. Insofar as anionic surfactants contain polyglycolether chains, they can have a conventional, preferably however a constricted, homologous distribution.

Examples of anionic surfactants as contemplated herein are, each in the form of sodium, potassium and ammonium salts, as well as mono-, di- and trialkanol ammonium salts having from about 2 to about 4 carbon atoms in the alkanol group,
  linear and branched fatty acids having about 8 to about 30 carbon atoms (soaps),
  ether carboxylic acids having the formula $R-O-(CH_2-CH_2O)_x-CH_2-COOH$, wherein R is a linear alkyl group having from about 8 to about 30 carbon atoms and x=0 or from about 1 to about 16,
  acyl sarcosides having from about 8 to about 24 carbon atoms in the acyl group,
  acyl tauride having from about 8 to about 24 carbon atoms in the acyl group,
  acylisethionates with from about 8 to about 24 carbon atoms in the acyl group, which are accessible through the esterification of fatty acids with the sodium salt of the 2-hydroxyethane sulfonic acid (isethionic acid), If fatty acids having from about 8 to about 24 carbon atoms, e.g. lauric, myristic, palimitic or stearic acid or also technical fatty acid fractions, e.g. the $C_{12}$-$C_{18}$ fatty acid fractions obtainable from coconut fatty acid are used for said esterification, the $C_{12}$-$C_{18}$ acylisethionates preferably suitable as contemplated herein are obtained, esters of tartaric acid and citric acid having alcohols, which are the addition products of from about 2-about 15 molecules of ethyl oxide and/or propylene oxide on fatty alcohols having from about 8 to about 22 carbon atoms, alkyl- and/or alkenyletherphosphates of the Formula $R^1(OCH_2CH_2)_n$—O—(PO—OX)—$OR^2$, in which $R^1$ preferably denotes an aliphatic hydrocarbon radical with from about 8 to about 30 carbon atoms, $R^2$ denotes hydrogen, a radical $(CH_2CH_2O)_nR^2$ or X, n denotes integers from 1 to about 10 and X denotes hydrogen, an alkali- or earth alkali metal or $NR^3R^4R^5R^6$, where $R^3$ to $R^6$ denote independently hydrogen or a $C_1$-$C_4$ hydrocarbon residue, sulfated fatty acid alkyleneglycolesters of the Formula $RCO(AlkO)_nSO_3M$, in which RCO denotes a linear or branched, aliphatic, saturated and/or unsaturated acyl radical with from about 6 to about 22 carbon atoms, Alk denotes $CH_2CH_2$, $CHCH_3CH_2$ and/or $CH_2CHCH_3$, n denotes numbers from about 0.5 to about 5 and M denotes a metal, such as an alkali metal, more particularly sodium, potassium, lithium, earth alkali metal, more particularly magnesium, calcium, zinc, or ammonium ion, such as $^+NR^3R^4R^5R^6$, with $R^3$ to $R^6$ denoting independently hydrogen or a C1-C4 hydrocarbon radical, monoglyceridesulfates and monoglycerideethersulfates of the Formula $R^8OC$—$(OCH_2CH_2)_x$—$OCH_2$—[CHO$(CH_2CH_2O)_yH$]—$CH_2O(CH_2CH_2O)_z$—$SO_3X$, in which $R^8CO$ denotes a linear or branched acyl radical with about 6 to about 22 carbon atoms, more particularly a linear acyl radical with from about 8 to about 22 carbon atoms, x, y and z in total denotes 0 or numbers from 1 to about 30, more preferably 2 to about 10, and X denotes an alkali- or earth alkali metal. Typical examples of monoglyceride (ether) sulfates suitable for the purposes of the present disclosure are the reaction products of lauric acid monoglyceride, coconut fatty acid monoglyceride, palmitic acid monoglyceride, stearic acid monoglyceride, oleic acid monoglyceride and tallow fatty acid monoglyceride, and their ethylene oxide adducts with sulfur trioxide or chlorosulfonic acid in the form of their sodium salts. Preferably, monoglyceride sulfates are used, wherein $R^8CO$ denotes a linear acyl radical having from about 8 to about 18 carbon atoms.

amide ether carboxylic acids, Formula $R^1$—CO—$NR^2$—$CH_2CH_2$—O—$(CH_2CH_2O)_nCH_2COOM$, with $R^1$ as straight-chained or branched alkyl- or alkenyl radical with a number of carbon atoms in the chain from 2 to about 30, n denotes an integer from 1 to about 20 and $R^2$ denotes hydrogen, a methyl-, ethyl-, propyl-, isopropyl-, n-butyl-, t-butyl- or iso-butyl radical and M stands for hydrogen or a metal such as an alkali metal, more particularly sodium, potassium, lithium, earth alkali metal, more particularly magnesium, calcium, zinc, or an ammonium ion, such as $^+NR^3R^4R^5R^6$, with $R^3$ to $R^6$ denoting independently hydrogen or a C1-C4 hydrogen radical. Such products can be obtained from the company Chem-Y, for example, under the product designation Akypo®, and acylglutamates of the Formula XOOC—CH2CH2CH(C(NH)OR)—COOX, in which RCO denotes a linear or branched acyl radical with from about 6 to about 22 carbon atoms and 0 and/or 1, 2 or 3 double bonds and X for hydrogen, an alkali and/or earth alkali metal, ammonium, alkylammonium, alkanolammonium or glucammonium.

The agent as contemplated herein can contain one or more amphoteric and/or zwitterionic surfactants. In the case of the zwitterionic surfactants, the hydrophilic molecule comprises a zwitterionic structural unit, i.e. a structural unit comprising both a cationically-charged and also an anionically-charged molecule. As contemplated herein, particularly suitable zwitterionic surfactants (b) are exemplified in that they have a cationically-charged molecule in the form of a quaternary ammonium group and their anionic molecule exists in the form of a grouping or —COO.

An ammonium group is quaternary when a type $(R_aR_b R_cR_dN)^+$ grouping exists, i.e. when all four H-atoms of the $NH_4$ ion from which the quaternary ammonium group is derived, is replaced by organic radicals R (and/or $R_a$ to $R_d$).

Particularly suitable zwitterionic surfactants include betaines, N-alkyl-N,N-dimethylammoniumglycinates, N-acyl-aminopropyl-N,N-dimethylammoniumglycinates, and 2-alkyl-3-carboxymethyl-3-hydroxyethyl-imidazolines.

Suitable agents as contemplated herein are also exemplified in that the agent additionally contains at least one amphoteric surfactant. Preferred amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkyl sarcosines, 2-alkylaminopropionic acids and alkylaminoacetic acids. Particularly preferred amphoteric surfactants are N-cocosalkylaminopropionate, cocosacylaminoethylaminopropionate and $C_{12}$-$C_{18}$ acylsarcosin.

It has also proved advantageous for the agent to contain other, non-ionogenic surfactants. Preferred non-ionic surfactants are alkyl polyglycosides as well as alkylene oxide binding agents to fatty alcohols, fatty acids and fatty acid glycerides with from about 2 to about 50 moles of ethylene oxide per mole of fatty alcohol or fatty acid. Preparations with outstanding properties are also obtained if they contain fatty acid esters of ethoxylated glycerol as nonionic surfactants. The most preferred embodiment is the agent containing as a non-ionic surfactant an ethoxylated castor oil with from about 2 to about 50 mol ethyleneoxide per mol of fatty acid or an ethoxylated, hydrated castor oil with from about 2 to about 50 mol ethyleneoxide per mol of fatty acid. The use of PEG-40 Castor Oil is most preferred in this context.

The agents as contemplated herein can contain one or more cationic surfactants. Cationic surfactants are surfactants, i.e. surfactant compounds, each having one or more positive charges. Cationic surfactants contain exclusively positive charges. Usually, said surfactants are made up of a hydrophobic part and a hydrophilic head group, wherein the hydrophobic part normally comprises a hydrocarbon frame (e.g. one or two linear or branched alkyl chains) and the positive charge(s) are localized in a hydrophilic head group. Cationic surfactants adsorb on boundary surfaces and aggregate in hydrous solutions above the critical micelle formation concentration to form positively charged micelles.

Examples of cation surfactants are quaternary ammonium bonds, which can carry, as hydrophobic radicals, one or two alkyl chains with a chain length of from about 8 to about 28 carbon atoms quaternary phosphonium salts, substituted with one or more alkyl chains with a chain length of from about 8 to about 28 C-atoms or Moreover, the cationic charging can also occur in the form of an onium structure component of a heterocyclical ring (e.g. of an imidazolium ring or a pyridinium ring).

In addition to the functional unit carried by the cationic charge, the cationic surfactants can also contain other uncharged functional groups, which is the case with esterquats, for example. As contemplated herein, preferred cationic surfactants are of the type of quaternary ammonium compounds, esterquats and amidoamines. Preferred quaternary ammonium compounds are ammonium compounds and ammonium halogenides, more particularly chlorides and bromides, such as alkyltrimethylammoniumchlorides, dialkyldimethylammoniumchlorides and trialkylmethylammoniumchlorides, e.g. cetyltrimethylammoniumchloride, stearyltrimethylammoniumchloride, distearyldimethylammoniumchloride, lauryldimethylammoniumchlorides, lauryldimethylbenzylammoniumchloride and tricetylmethylammoniumchloride, as well as the imidazolium compounds known under the INCI trade names of Quaternium-27 and Quaternium-83. The long alkyl chains of the aforementioned surfactants preferably have from about 10 to about 18 carbon atoms.

Esterquats are known substances containing both at least one ester function and at least one quaternary ammonium group as the structural element. Preferred esterquats are quaternated ester salts of fatty acids with triethanolamine, quaternated ester salts of fatty acids with diethanolalkyl amines and quaternated ester salts of fatty acids with 1,2-dihydroxypropyldialkylamines. The alkylamidoamines are usually produced through the amidation of natural or synthetic fatty acids and fatty acid molecules with dialkylaminoamines. A most preferred compound from this substance group as contemplated herein is the stearamidopropyldimethylamine commercially available under the trade name of Tegoamid® S 18. As contemplated herein, the quaternized protein hydrolysates can also be used.

The anionic, amphoteric, zwitterionic, non-ionic and cationic surfactants may be contained in a total quantity of from about 0.1 to about 15.0 wt. %, preferably from about 0.2 to about 12.0 wt. %, more preferably from about 1.25 to about 10.0 wt. % and most preferably from about 1.50 to about 9.0 wt. %—calculated based on the total weight of the agent in each case.

It has also emerged that the use of polyols promotes the decolorizing effect. For this reason, the decolorizing agent as contemplated herein preferably contains one or more polyols.

A polyol is a compound having at least two aliphatic (i.e. non-phenolic) OH groups.

Examples of suitable polyols as contemplated herein are, in particular, ethylengylcol, 1,2-propylenglycol, 1,3-propandiol, 1,2-butandiol, 1,3-butandiol, 1,2-pentandiol, 1,3-pentandiol, 1,4-pentandiol, 1,5-pentandiol, 1,2-hexandiol, 1,3-hexandiol, 1,4-hexandiol, 1,5-hexandiol and 1,6-hexandiol. Polyethyleneglycol and polypropyleneglycol, however, are also suitable.

In another embodiment, a decolorizing agent as contemplated herein is exemplified in that it additionally contains one or more polyols from the group of ethylenegylcol (1,2-ethanediol), 1,2-propanediol, 1,3-propanediol, 1,2-butanediol, 1,3-butanediol, 1,4-butanediol, 1,2-pentanediol, 1,3-pentanediol, 1,4-pentanediol, 1,5-pentanediol, 1,2-hexanediol, 1,3-hexanediol, 1,4-hexanediol, 1,5-hexanediol, 1,6-hexanediol, polyethyleneglycol, and polypropyleneglycol.

The polyols are preferably contained in the agents as contemplated herein in a total quantity of from about 0.5 to about 15.0 wt. %, more preferably from about 2.5 to about 13.5 wt. %, even more preferably from about 3.5 to about 11.5 wt. %, and most preferably from about 4.5 to about 9.5 wt. %, relative to the total weight of the cosmetic agent.

pH Value

It has emerged that the decolorizing agents as contemplated herein most preferably has a pH value in the range from about 7.5 to about 12.5. During the work that led to this present disclosure, it emerged that the pH value for achieving a particularly strong decolorizing effect is a key determinant.

A decolorizing effect was also achieved by employing acidically or neutrally set agents. However, it was observed that the strongest decolorizing effect is achieved by treating the hair with an agent set to a pH value above about 7.5, preferably above about 8.0, and more preferably above about 8.5. However, setting pH values above about 11.0 is avoided in order to prevent excessive hair damage and also increased skin irritation.

In another most preferred embodiment, a method as contemplated herein is exemplified in that an agent, which contains water and which has a pH value in the range from about 7.5 to about 12.5, preferably from about 8.0 to about 10.5 and more preferably from about 8.5 to about 10.0, is applied to the keratin fibers.

The pH value can be measured by employing a gas electrode, for example, which is usually commercially available in the form of a combination electrode. Before the pH value is measured, the gas electrodes are usually calibrated with calibration solutions of a known pH value. The pH values as defined by the present disclosure are pH values that were measured at a temperature of 22° C.

The desired pH value can be set by employing various alkalizing agents. Suitable alkalizing agents as contemplated herein are selected from the group formed from ammonia, alkanolamines, alkali metal hydroxides, alkali metal metasilicates, alkalimetal phosphates and alkali metal hydrogen phosphates. Preferred inorganic alkalizing agents are sodium hydroxide, potassium hydroxide, sodium silicate and sodium metasilicate. Organic alkalizing agents usable as contemplated herein are preferably selected from monoethanolamine, 2-amino-2-methylpropanol and triethanolamine. The basic amino acids that can likewise be used as alkalizing agents are preferably selected from the group formed of arginine, lysine, ornithine, and histidine.

Although the hair treatment agents as contemplated herein are preferably set to pH values in the alkali range, it may be necessary to also use small quantities of acidification agents in order to finely adjust the pH value. Acidification agents suitable as contemplated herein include citric acid, lactic acid, acetic acid and diluted mineral acids (such as hydrochloric acid, sulfuric acid, phosphoric acid).

Oxidation Dye Precursors and/or Partially-Oxidizing Dyes

The method as contemplated herein involves the use of agents in order to decolorize the previously dyed human keratin fibers. The dyed keratin fibers are fibers which have been colored beforehand by employing conventional oxidative dyes and/or partially oxidative dyes known to a person skilled in the art.

The decoloration agents are suitable for removing colors produced on the keratinous fibers by employing oxidizing dyes based on developer and coupler components. If the following compounds were used as developers, the colors thus produced can easily be removed effectively and almost without subsequent post-darkening by employing the decoloration agent: p-phenylenediamine, p-toluenediamine, N,N-bis-(β-hydroxyethyl)-p-phenylenediamine, 4-N,N-bis-(β-hydroxyethyl)-amino-2-methylaniline, 2-(β-hydroxyethyl)-p-phenylenediamine, 2-(α,β-dihydroxyethyl)-p-phenylenediamine, 2-hydroxymethyl-p-phenylenediamine, bis-(2-hydroxy-5-aminophenyl)-methane, p-aminophenol, 4-amino-3-methylphenol, 2,4,5,6-tetraaminopyrimidine, 4-hydroxy-2,5,6-triaminopyrimidine, 2-hydroxy-4,5,6-triaminopyrimidine and/or 4,5-diamino-1-(β-hydroxyethyl)-pyrazol.

If the following compounds were used as couplers, the colors produced thereby can likewise be removed with very good decoloration results: m-phenylenediamine derivates, naphthols, resorcin and resorcin derivates, pyrazolone and m-aminophenol derivatives. Particularly suitable coupler substances are 1-naphthol, 1,5-, 2,7- and 1,7-dihydroxy naphthalene, 5-amino-2-methylphenol, m-aminophenol, resorcinol, resorcinol monomethylether, m-phenylenediamine, 1-phenyl-3-methyl-pyrazolone-5, 2,4-dichlor-3-aminophenol, 1,3-bis-(2',4'-diaminophenoxy)-propane, 2-chlor-resorcinol, 4-chlor-resorcinol, 2-chlor-6-methyl-3-aminophenol, 2-amino-3-hydroxypyridine, 2-methylresorcinol, 5-methyl resorcinol and 2-methyl-4-chlor-5-aminophenol, 1-naphthol, 1,5-dihydroxynaphthaline, 2,7-dihydroxynaphthaline, 1,7-dihydroxynaphthaline, 3-aminophenol, 5-amino-2-methylphenol, 2-amino-3-hydroxypyridine, resorcinol, 4-chlororesorcinol, 2-chlor-6-methyl-3-aminophenol, 2-methylresorcinol, 5-methylresorcinol, 2,5-dimethylresorcinol and 2,6-dihydroxy-3,4-dimethylpyridine. Certain dyes and/or dye combinations can be removed particularly well and particularly completely by applying dithiols of the Formula (I).

It has emerged, for example, that the natural tints otherwise known for their durability and resistance can be decolorized particularly well if at least one dithiol of the Formula (I) is used in the method.

The decolorizing effect was extremely effective on hair that had been dyed by employing one of the following combinations of developers/couplers: p-toluenediamine/resorcin, p-toluenediamine/2-methyl resorcin, p-toluenediamine/4-chlororesorcin, p-toluenediamine/m-aminophenol, N,N-bis-(β-hydroxyethyl)-p-phenylenediamin/resorcin, N,N-bis-(β-hydroxyethyl)-p-phenylenediamine/2-methylresorcin, N,N-bis-(β-hydroxyethyl)-p-phenylenediamine/4-chlororesorcin, N,N-bis-(β-hydroxyethyl)-p-phenylenediamine/m-aminophenol,2-(β-hydroxyethyl)-p-phenylenediamine/resorcin, 2-((3-hydroxyethyl)-p-phenylenediamine/2-methylresorcin, 2-(β-hydroxyethyl)-p-phenylenediamine/4-chlororesorcin and/or 2-(β-hydroxyethyl)-p-phenylenediamine/m-aminophenol.

In another most preferred embodiment, a method as contemplated herein is exemplified in that the keratin fibers were previously dyed by employing an agent containing at least one of the following combinations: p-toluenediamine/resorcin, p-toluenediamine/2-methylresorcin, p-toluenediamine/4-chlororesorcin, p-toluenediamine/m-aminophenol, N,N-bis-(β-hydroxyethyl)-p-phenylenediamine/resorcin, N,N-bis-(β-hydroxyethyl)-p-phenylenediamine/2-methylresorcin, N,N-bis-(β-hydroxyethyl)-p-phenylenediamine/4-chlororesorcin, N,N-bis-(β-hydroxyethyl)-p-phenylenediamine/m-aminophenol,2-(β-hydroxyethyl)-p-phenylenediamine/resorcin, 2-(β-hydroxyethyl)-p-phenylenediamine/2-methylresorcin, 2-(β-hydroxyethyl)-p-phenylenediamine/4-chlororesorcin and/or 2-(β-hydroxyethyl)-p-phenylenediamine/m-aminophenol.

The decolorizing agents as contemplated herein are designed to remove said colors and therefore themselves preferably contain no dyes, more particularly no oxidative dye precursors of the developer type and/or coupler type, as well as partially-oxidizing dyes.

In another most preferred embodiment, a method as contemplated herein is exemplified in that an agent, wherein the total quantity of all partially-oxidizing dyes and oxidation dye precursors is a value of maximum 0.2 wt. %, preferably maximum 0.1 wt. %, more preferably maximum 0.05 wt. % and most preferably maximum 0.01 wt. %—relative to the total weight of the agent—is applied to the dyed keratin fibers.

Method Steps

As part of the method as contemplated herein, carrying out the following steps has proven particularly suitable.

A method for the dyeing and reductive decolorization of human keratin fibers, comprising the following steps in the stated sequence, is most preferred (i) Application of a cosmetic colorant containing at least one partially oxidizing dye and/or at least one oxidative dye precursor to keratinous fibers (ii) Allowing the colorant to take effect for a period of from about 5 to about 60 minutes (iii) Rinsing out the colorant (iv) Applying a decolorizing agent to the keratin fibers, (a) which contain, in a cosmetic carrier, at least one compound of the Formula (I)

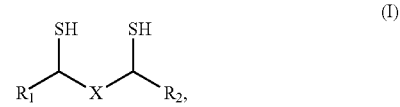

wherein

R1, R2 denote independently of one another a hydrogen atom, a carboxy group (—COOH) or the salt thereof, a $C_1$-$C_6$ alkyl group, a hydroxy $C_1$-$C_6$ alkyl group, or a $C_1$-$C_6$ alkoxy-carbonyl group, X denotes a bivalent organic radical of the Formula (II) or a direct bond,

R3 denotes a hydroxy group, a hydrogen atom, a carboxy group (—COOH) or the salt thereof, a $C_1$-$C_6$ alkoxy-carbonyl group, a $C_1$-$C_6$-alkyl group or an amino group, and n denotes an integer from 1 to 4, and (b) the total content of sulfur-containing compounds, which are not the same as the compounds of Formula (I), is below about 1.0 wt. %, wherein the total content is relative to the total weight of the agent.

(v) Allowing the decolorant to take effect for a period of from about 5 to about 60 minutes, preferably from about 10 to about 55 minutes, more preferably from about 15 to about 55 minutes, most preferably from about 20 to about 50 minutes, (vi) Rinsing out the decolorization agent, Steps (i), (ii) and (iii) of the method constitute the coloration process of the keratin fibers and are therefore executed in a direct temporal sequence in succession. In principle, there is no time limitation for the sequence of steps (iii) and (iv). For example, step (iv) can take place hours, days or even six weeks after step (iv) is complete.

However, the method is intended to remove the unwanted color result of the coloring process in steps (i) to (iii). Therefore, it is obvious that the decoloration can take place only when the colored fibers show the unwanted color result. If the keratin fibers were colored with partially oxidizing dyes, for example, and this color has completely washed out after 2 weeks, a subsequent decolorization process is neither necessary nor addressed by the present disclosure.

In step (iv) of the method, a decolorizing agent is applied to the keratin fibers. Steps (iv), (v) and (vi) of the method constitute the decolorizing process of the keratin fibers and are therefore executed in a direct temporal sequence in succession.

To further enhance the effect and/or accelerate the decolorization process, step (v) can also be executed with the aid of warmth or heat. A corresponding heating of the keratin fibers to which the decolorizing agent is applied can be achieved by using a hood, a dryer hood or a hairdryer.

Usage

During the work leading to this present disclosure, it emerged that the compounds of the Formula (I) described above in detail are suitable for decolorizing effectively and significantly colored hair. The decolorizing effect thus achieved is long-lasting and a post-darkening of the reductively decolorized keratin fibers was able to be effectively prevented.

A further subject matter of the present disclosure is therefore the use of compounds of the formula (I)

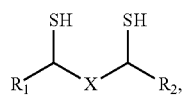
(I)

wherein
R1, R2 denote, independently of one another, a hydrogen atom, a carboxy group (—COOH) or the salt thereof, a $C_1$-$C_6$ alkyl group, a hydroxy $C_1$-$C_6$ alkyl group, or a $C_1$-$C_6$ alkoxy-carbonyl group,
X denotes a bivalent organic radical of the Formula (II) or a direct bond,

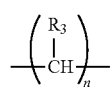
(II)

R3 denotes a hydroxy group, a hydrogen atom, a carboxy group (—COOH) or the salt thereof, a $C_1$-$C_6$ alkoxy-carbonyl group, a $C_1$-$C_6$-alkyl group or an amino group, and
n denotes an integer from 1 to 4.
for decolorizing human keratin fibers, which were dyed by employing oxidation dyes and/or partially-oxidizing dyes.

With respect to other preferred embodiments of the method as contemplated herein, the method mentioned in the present disclosure apply mutatis mutandis.

Kit-of-Parts

For the application, the decolorizing agent as contemplated herein is preferably set to the pH value at which is develops its greatest effect. For storage purposes, however, it may be preferable to select the pH value at which the dithio compound of the Formula (I) is most stable. Since the pH values suitable for storage and application usually differ, changing the pH value of the decolorizing agent shortly before application can be particularly advantageous.

The pH value of the decolorizing agent can be changed, for example, by mixing at least two agents, wherein the first agent (Preparation (A)) contains at least one dithio compound of the Formula (I) and the second agent (Preparation (B)) is hydrous and contains at least one acidification agent (i.e. an acid) and/or at least one alkalizing agent.

The first agent (Preparation (A)), which contains the dithio compound, can in turn be a hydrous agent, the agent can however likewise be packaged in an anhydrous manner, by the at least one dithio compound of the Formula (I) being integrated into a hydrous, oily carrier or a fat-containing paste, or by packaging the dithio compound of the Formula (I) in the form of a powder or a pressed solid body, for example.

The two components required to produce the ready-to-use agent are practically provided to the user in the form of a kit (i.e. a kit-of-parts), which comprises at least two Preparations (A) and (B) packaged separately from one another. The ready-to-use decolorizing agent can be produced by mixing Preparations (A) and (B).

A further subject matter of the present disclosure is therefore a kit-of-parts for decolorizing human keratin fibers, which were dyed with oxidation dyes and/or partially-oxidizing dyes, comprising at least two Preparations (A) and (B) packaged separately from one another, wherein
the first Preparation (A) contains, in a cosmetic carrier, at least one compound of the Formula (I), as disclosed in detail in the description of the first subject matter of the present disclosure, and
the second Preparation (B) is hydrous and contains at least one acid and/or at least one alkalizing agent.

In other words, this subject matter of the present disclosure is a kit-of-parts for decolorizing human keratin fibers, which were dyed with oxidation dyes and/or partially-oxidizing dyes, comprising at least two Preparations (A) and (B) packaged separately from one another, wherein
the first Preparation (A) contains, in a cosmetic carrier, at least one compound of the Formula (I)

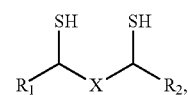
(I)

wherein
R1, R2 denote, independently of one another, a hydrogen atom, a carboxy group (—COOH) or the salt thereof, a $C_1$-$C_6$ alkyl group, a hydroxy $C_1$-$C_6$ alkyl group, or a $C_1$-$C_6$ alkoxy-carbonyl group,
X denotes a bivalent organic radical of the Formula (II) or a direct bond,

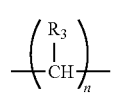
(II)

R3 denotes a hydroxy group, a hydrogen atom, a carboxy group (—COOH) or the salt thereof, a $C_1$-$C_6$ alkoxy-carbonyl group, a $C_1$-$C_6$-alkyl group or an amino group, and n denotes an integer from 1 to 4, and
the second Preparation (B) is hydrous and contains at least one acid and/or at least one alkalizing agent.

As described above, it is particularly preferable if in the Preparation (A), the total content of sulfur-containing compounds, which are different to the compounds of the Formula (I), is below about 1.0 wt. %, of preferably below about 0.5 wt. %, more preferably below about 0.1 wt. % and most preferably below about 0.05 wt. %, wherein the total content is relative to the total weight of the Preparation (A).

It is also particularly preferable if in the Preparation (B), the total content of sulfur-containing compounds, which are different to the compounds of the Formula (I), is below about 1.0 wt. %, or preferably below about 0.5 wt. %, more preferably below about 0.1 wt. % and most preferably below about 0.05 wt. %, wherein the total content is relative to the total weight of the Preparation (B).

Acids in Preparation (B) can include one or more acids from the group of citric acid, tartaric acid, malic acid, lactic acid, acetic acid, sulfuric acid, hydrochloric acid, phosphoric acid, methane sulfonic acid, benzoic acid, malonic acid, oxalic acid, pyruvic acid, oxaloacetic acid (oxobutanoic acid) and/or 1-hydroxyethane-1,1-diphosphonic acid.

In a further embodiment, a kit-of-parts as contemplated herein is exemplified in that the Preparation (B) contains at least one acid from the group of citric acid, tartaric acid, malic acid, lactic acid, acetic acid, sulfuric acid, hydrochloric acid, phosphoric acid, methane sulfonic acid, benzoic acid, malonic acid, oxalic acid, pyruvic acid, oxaloacetic acid (oxobutanoic acid) and/or 1-hydroxyethane-1,1-diphosphonic acid.

It is also most preferable for the second Preparation (B) to be hydrous and contain at least one alkalizing agent.

The alkalizing agents described above are particularly suitable alkalizing agents, i.e. suitable alkalizing agents can be selected from the group formed from ammonia, alkanolamines, basic amino acids, as well as inorganic alkalizing agents such as (earth-)alkali metal hydroxides, (earth-)alkali metal metasilicates, (earth-)alkali metal phosphates and (earth-)alkali metal hydrogen phosphates. Preferred inorganic alkalizing agents are sodium hydroxide, potassium hydroxide, sodium silicate and sodium metasilicate. Organic alkalizing agents usable as contemplated herein are preferably selected from monoethanolamine, 2-amino-2-methylpropanol and triethanolamine. The basic amino acids that can likewise be used as alkalizing agents are preferably selected from the group formed of arginine, lysine, ornithine, and histidine.

In a preferred embodiment, the Preparation (B) of the kit-of-parts is a hydrous preparation with a water content of from about 5.0 to about 99.0 wt. %, preferably from about 15.0 to about 98.0 wt. %, more preferably from about 50-about 98 wt. %. The calculation basis for the water content stated in wt. % is the weight quantity of water contained in the total weight of the agent. The pH value of the Preparation (B) can be a value from about 7.5 to about 12.5, preferably from about 8.0 to about 10.5, more preferably from about 8.5 to about 11.0.

The Preparation (B) is mixed with the Preparation (A) to produce the ready-to-use decolorizing agent, wherein the Preparation (A) with the dithiols of the Formula (I) contains at least one reducing agent. To avoid incompatibilities and uncontrollable reactions, the Preparation (B) is therefore preferably free of all substance classes, which can enter into unwanted reactions with the reducing agents. It is particularly advantageous for the Preparation (B) to be free of oxidants.

In another most preferred embodiment, a kit-of-parts as contemplated herein is exemplified in that the total quantity of all the oxidants contained in the Preparation (B) from the group of peroxo compounds is maximum of about 0.2 wt. %, preferably from a maximum of about 0.1 wt. %, more preferably from a maximum of about 0.05 wt. % and most preferably from a maximum of about 0.01 wt. %—relative to the total weight of the Preparation (B).

To avoid the aforementioned incompatibilities, the Preparation (A) is preferably free of oxidants. In another most preferred embodiment, a kit-of-parts as contemplated herein is exemplified in that the total quantity of all the oxidants contained in the Preparation (A) from the group of peroxo compounds is a maximum of about 0.2 wt. %, preferably from a maximum of about 0.1 wt. %, more preferably from a maximum of about 0.05 wt. % and most preferably from a maximum of about 0.01 wt. %—relative to the total weight of the Preparation (A). Peroxo compounds according to this present disclosure are more particularly hydrogen peroxide, sodiumperoxydisulfate potassium peroxodisulfate and ammonium peroxodisulfate.

The ready-to-use decolorizing agent can be produced by mixing Preparations (A) and (B). In principle, the Preparations (A) and (B) can be mixed in various mixing ratios, such as (A)/(B) from about 20:1 to about 1:20. The Preparations (A) and (B) are preferably mixed with one another in a mixing ratio of from about 1:10 to about 10:1, more preferably from about 1:2 to about 2:1. The mixing ratios indicate the ratio of the total quantities of the Preparations (A) and (B) relative to one another.

The Preparations (A) and (B) are packaged separately from one another and can exist packaged in a container suitable for the purpose. Suitable containers include glass, or more particularly, plastic bottles, jars, tubes or other suitable containers.

To produce the ready-to-use mixture, the agent (A) can be transferred from Container (I) completely to Container (II)—which already contains the agent (B). In this case, the size of Container (II) is selected such that Container (II) can receive the total quantity of the Preparations (A) and (B) and also allows the two agents (A) and (B) to be mixed by shaking or stirring, for example.

Likewise, the mixture can also be produce by completely transferring agent (B) from Container (II) to Container (I)—which already contains the agent (A). In this case, the size of Container (I) should be selected such that Container (I) can receive the total quantity of the Preparations (A) and (B) and also allows the two agents (A) and (B) to be mixed by shaking or stirring, for example.

Another possibility of producing the application mixture is to completely transfer both agents (A) and (B) from Containers (I) and (II) to a third container, which then allows the two agents to be mixed by shaking or stirring, for example.

Example: A Kit-of-Parts as Contemplated Herein Contains 100 g of Preparation (A) in Container (I)
50 g of Preparation (B) in Container (II)
To produce the ready-to-use mixture, Preparation (B) is completely transferred from Container (II) to Container (I).

Preparations (A) and (B) are then shaken or stirred with one another. The mixture ratio of Preparations (A)/(B) is at a value of (100 g/50 g)=2:1.

The kit-of-parts can also comprise a third, separately packaged Preparation (C). This is the case in particular if Component (A) containing the compound of the Formula (I) is to be packaged in an anhydrous manner.

Other Constituents

The method as contemplated herein and the agent used in the kit-of-parts according to the present disclosure can also contain additional active ingredients, adjuvants and additives in order to improve the decoloration effect and set further desired properties of the agent. Examples are one or more agents of additional non-ionic polymers, such as vinylpyrrolidinon/vinylacrylat-copolymers, polyvinylpyrrolidinon, vinylpyrrolidinon/vinylacetate-copolymers, polyethylenglycols and polysiloxanes; additional silicones such as volatile or non-volatile, straight-chained, branched or cyclical, cross-linked or non-cross-linked polyalkylsiloxanes (such as dimethicones or cyclomethicones), polyarylsiloxanes and/or polyalkylarylsiloxanes, more particularly polysiloxanes with organofunctional groups such as substituted or unsubstituted amines (amodimethicones), carboxyl-, alkoxy- and/or hydroxyl groups (dimethiconcopolyols), linear polysiloxan(A)-polyoxyalkylen(B)-block copolymers, grafted silicon polymers; cationic polymers such as quaternized cellulose ether, polysiloxanes with quaternary groups, dimethyldiallylammoniumchloride-polymers, acrylamid-dimethyldiallyl-ammonium chloride copolymers, with diethyl sulfate quaternated dimethylaminoethylmethacrylat-vinylpyrrolidinon-copolymers, vinylpyrrolidinon-imidazolinium-methochloride-copolymers and quaternated polyvinylalcohol; zwitterionic and amphoteric polymers; anionic polymers such as polyacryl acids or cross-linked polyacryl acids; structurants, such as glucose, malic acid and lactic acid, hair-conditioning compounds such as phospholipides, for example lecithin and cephalin; perfume oils, dimethylisosorbid and cyclodextrine; fiber structure-improving agents, more particularly mono-, di- and oligosaccharides, such as glucose, galactose, fructose, fruit sugar and lactose; dyes for coloring the preparations; anti-dandruff active ingredients such as piroctone olamine, zinc omadine and climbazol; amino acids and oligopeptides; protein hydrolysates on an animal and/or plant basis, as well as in the form of their fatty acid condensation products or, where applicable, anionically or cationically modified derivatives; plant oils; light stabilizers and UV blockers; active ingredients such as panthenol, pantothenic acid, pantolacton, allantoin, pyrrolidinoncarbonic acids and the salts thereof, as well as bisabolol; polyphenols, more particularly hydroxy cinnamic acids, 6,7-dihydroxycumarines, hydroxybenzoic acids, catechins, tannins, flavanons, anthocyanidines, flavanons, flavons and flavonols; ceramides or pseudoceramides; vitamins, provitamins and vitamin precursors; plant extracts; fats and waxes such as fatty alcohols, beeswax, montan wax and paraffins; source and penetration substances such as glycerin, propyleneglycolmonoethylether, carbonate, hydrogen carbonate, guanidine, urea, as well as primary, secondary and tertiary phosphates; opacifiers such as latex, styrene/PVP and styrene/acrylamide copolymers; pearl shine concentrates such as ethyleneglycolmono- and -distearate as well as PEG-3-distearate; pigments as well as propellants such as propane-butane-mixtures, $N_2O$, dimethylether, $CO_2$ and air. In this context, explicit reference is made to the known monographies, e.g. Kh. Schrader, Grundlagen and Rezepturen der Kosmetika [Cosmetic principles and formulas, 2nd Edition], Hüthig Buch Verlag, Heidelberg, 1989, which reflect the corresponding knowledge of a person skilled in the art.

Each of the aforementioned further ingredients can—relative to the total weight of the agent concerned—can be used in a quantity of from about 0.01 to about 20 wt. %, for example.

EXAMPLES 1.1. Coloration

The following formulations were produced (all data in wt. %):

Dye cream (F1)

| Raw material | wt. % |
| --- | --- |
| Cetearyl alcohol | 6.6 |
| C12-C18 fatty alcohols | 2.4 |
| Ceteareth-20 | 0.6 |
| Ceteareth-12 | 0.6 |
| Plantacare 1200 UP (laurylglucoside, 50-53% hydrous solution) | 2.0 |
| Sodium laureth-6 carboxylate (21% i hydrous solution) | 10.0 |
| Sodium myreth sulfate (68-73% hydrous solution) | 2.8 |
| Sodium acrylate, trimethylammoniopropylacrylamide chloride copolymer (19-21% hydrous solution) | 3.8 |
| Sodium hydroxide | 0.26 |
| p-toluenediamine, sulfate | 0.48 |
| m-Aminophenol | 0.02 |
| 4-chlororesorcin | 0.09 |
| 2-Methyl resorcin | 0.04 |
| Resorcin | 0.12 |
| Ammonium sulfate | 0.71 |
| Sodium sulfate | 0.4 |
| Ascorbic acid | 0.1 |
| 1-Hydroxyethane-1,1-diphosphonic acid (60% hydrous solution) | 0.2 |
| Sodium soluble glass | 0.5 |
| L-Serin | 1.0 |
| Ammonia (25% hydrous solution) | 6.7 |
| Water | ad 100 |

Oxidant (Ox)

| Raw material | wt. % |
| --- | --- |
| Sodium benzoate | 0.04 |
| Dipicolinic acid | 0.1 |
| Di-sodium pyrophosphate | 0.1 |
| Potassium hydroxide | 0.09 |
| 1,2-Propyleneglycol | 1.0 |
| 1-Hydroxyethane-1,1-diphosphonic acid (60% hydrous solution) | 0.25 |
| Paraffinum Liquidum | 0.30 |
| Steartrimonium chloride | 0.39 |
| Cetearyl alcohol | 3.4 |
| Ceteareth-20 | 1.0 |
| Hydrogen peroxide (50% hydrous solution) | 12.0 |

The dye cream (F1) and the oxidant (Ox) were then mixed together in a ratio of 1:1 and applied to the hair strands (Kerling Euro natural hair, white). The weight ratio of the application mixture:Hair 4:1, exposure time 30 minutes at a temperature of 32 degrees Celsius. The strands were then rinsed with water, dried and left to rest at room temperature for at least 24 hours. The hair strands were then measured by colometry.

The dye (F1+OX) colored the strands with a hazelnut brown tint.

1.2. Decolorization

The following decolorizing agents were produced (all data in wt. %)

|  | V1 | E1 | E2 |
|---|---|---|---|
| Dithioerythritol (erythro-1,4-Dimercapto-2,3-butandiol) | — | 2.0 | — |
| Dthiothreitol (1,4-Dimercapto-2,3-butandiol) | — | — | 2.0 |
| Rongalit (sodium hydroxy methane sulfinate) | 10.0 | — | — |
| pH | 4.5 | 8.5 | 8.5 |
| Water | ad 100 | ad 100 | ad 100 |

The dyed hair strands were each decolorized by employing the decolorizing agent for 30 minutes at room temperature. The strands were then rinsed out with water and dried overnight. The hair strands were then measured by colometry again.

The decoloration result was assessed by determining the ΔE value each formulation was tested on 3 strands, and each strand was measured at 4 measuring points by colorimetry. The mean value was formed from these individual values.

From the L*a*b* values obtained, the color distance (ΔE value) between the dyed and the decolorized strands was determined by employing the CIELAB2000 formula. The higher the ΔE value, the better the decolorization results.

| Decolorization after 24 hours | V1 | E1 | E2 |
|---|---|---|---|
| ΔE value (dyed - decolorized) | 8.7 | 11.4 | 8.2 |

The decolorized strands were then stored in air for a further 72 hours and then measured again by colorimetry. The ΔΔE value is the difference (i.e. the color distance) between the dyed hair strands, which were measured after 24 hours and after 72 hours. The higher the ΔΔE value, the stronger the post-darkening effect. A strong post-darkening effect is not desired.

| Decolorization after 72 hours | V1 | E1 | E2 |
|---|---|---|---|
| ΔE value (dyed - decolorized) | 5.3 | 10.9 | 8.0 |
| ΔΔE value (post-darkening) | 3.4 | 0.5 | 0.2 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for decolorizing human keratin fibers, which were dyed with oxidation dyes, comprising:
    applying a cosmetic colorant comprising an oxidative dye precursor to the human keratin fibers;
    allowing the cosmetic colorant to take effect for a period of time of from about 5 to about 60 minutes;
    rinsing out the cosmetic colorant;
    applying an agent to the dyed keratin fibers, wherein the agent comprises;
        (a) from about 0.1 to about 30.0 wt. % of 1,4-dimercapto-2,3-butanediol in a cosmetic carrier, and wherein;
        (b) the total content of sulfur-containing compounds, which are not the 1,4-dimercapto-2,3-butanediol, is below about 1.0 wt. %, wherein the total content is relative to a total weight of the agent.

2. The method according to claim 1, wherein the agent comprises a total content of sulfur-containing compounds of which are different than the 1,4-dimercapto-2,3-butanediol, is below about 0.5 wt. %, the total content being relative to a total weight of the agent.

3. The method according to claim 1, wherein the agent comprises at least one surfactant selected from the group consisting of anionic, amphoteric, zwitterionic, non-ionic and cationic surfactants.

4. The method according to claim 1, wherein the agent comprises water and wherein the agent has a pH value in the range from about 7.5 to about 12.5.

5. The method according to claim 1, wherein applying the cosmetic colorant comprises at least one of the following combinations selected from the group consisting of p-toluenediamine/resorcin, p-toluenediamine/2-methylresorcin, p-toluenediamine/4-chlororesorcin, p-toluenediamine/m-aminophenol, N,N-bis-(β-hydroxyethyl)-p-phenylenediamine/resorcin, N,N-bis-(β-hydroxyethyl)-p-phenylenediamine/2-methylresorcin, N,N-bis-(β-hydroxyethyl)-p-phenylenediamine/4-chlororesorcin, N,N-bis-(β-hydroxyethyl)-p-phenylenediamine/m-aminophenol, 2-(β-hydroxyethyl)-p-phenylenediamine/resorcin, 2-(β-hydroxyethyl)-p-phenylenediamine/2-methylresorcin, 2-(β-hydroxyethyl)-p-phenylenediamine/4-chlororesorcin and 2-(β-hydroxyethyl)-p-phenylenediamine/m-aminophenol.

6. The method according to claim 1 wherein, relative to a total weight of the agent, the 1,4-dimercapto-2,3-butanediol is from about 0.2 to about 20.0 wt. %.

7. The method according to claim 1 wherein, relative to a total weight of the agent, the 1,4-dimercapto-2,3-butanediol is from about 0.3 to about 10.0 wt. %.

8. The method according to claim 1 wherein, relative to a total weight of the agent, the 1,4-dimercapto-2,3-butanediol is from about 0.5 to about 6.0 wt. %.

9. The method according to claim 1 wherein the total content of sulfur-containing compounds, which are different than the 1,4-dimercapto-2,3-butanediol, is below about 0.1 wt. %, the total content being relative to a total weight of the agent.

10. The method according to claim 1 wherein the total content of sulfur-containing compounds, which are different than the 1,4-dimercapto-2,3-butanediol, is below about 0.05 wt. %, the total content being relative to a total weight of the agent.

* * * * *